US007933440B2

(12) United States Patent
Littmann

(10) Patent No.: US 7,933,440 B2
(45) Date of Patent: Apr. 26, 2011

(54) METHOD AND SYSTEM FOR EVALUATING TWO TIME-SEPARATED MEDICAL IMAGES

(75) Inventor: Arne Littmann, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 971 days.

(21) Appl. No.: 11/769,821

(22) Filed: Jun. 28, 2007

(65) Prior Publication Data

US 2008/0159607 A1 Jul. 3, 2008

(30) Foreign Application Priority Data

Jun. 28, 2006 (DE) .................. 10 2006 029 718

(51) Int. Cl.
*G06K 9/00* (2006.01)
*G06K 9/64* (2006.01)
*A61B 5/05* (2006.01)
*A61B 6/00* (2006.01)

(52) U.S. Cl. ........ 382/131; 382/278; 382/128; 600/410; 378/4; 378/21

(58) Field of Classification Search .................. 382/128, 382/131, 278, 288, 199; 378/4, 21; 600/410, 600/415, 419
See application file for complete search history.

(56) References Cited

U.S. PATENT DOCUMENTS

| | | | |
|---|---|---|---|
| 5,467,404 A * | 11/1995 | Vuylsteke et al. | 382/274 |
| 6,067,373 A * | 5/2000 | Ishida et al. | 382/130 |
| 6,252,931 B1 * | 6/2001 | Aach et al. | 378/98.2 |
| 6,268,611 B1 * | 7/2001 | Pettersson et al. | 250/559.3 |
| 6,292,683 B1 * | 9/2001 | Gupta et al. | 600/410 |
| 6,421,552 B1 * | 7/2002 | Hsieh | 600/425 |
| 6,553,152 B1 * | 4/2003 | Miller et al. | 382/294 |
| 6,690,824 B1 * | 2/2004 | Stringa | 382/176 |

(Continued)

FOREIGN PATENT DOCUMENTS

WO    WO 02/101407    12/2002

OTHER PUBLICATIONS

Bartlett et al. "Interactive Segmentation of Cerebral Gray Matter, white matter and CSF: Photographic and MR Images" Computerized Medical Imaging and Graphics, vol. 18, Issue 6, Nov.-Dec. 1994, pp. 449-460.*

(Continued)

*Primary Examiner* — Jingge Wu
*Assistant Examiner* — Mia M Thomas
(74) *Attorney, Agent, or Firm* — Schiff Hardin LLP

(57) ABSTRACT

In a method for evaluation of two images of an organ system acquired at different points in time to establish a pathological variation, the organ system exhibits a first region and a second region that are present in and that are differentiated in each of the images, with the second region of the pathological variation being acquired more strongly than the first region. A registration is determined that causes the respective first region in two images to be in registration with each other. Imaging system-dependent differences, in particular deformations, are determined and compensated between the two images. After an extension of the registration such that the second region is encompassed as well by the extended registration, via a transformation one of the two images to the other can be made, presented and/or stored that includes the second region, using the extended registration. A medical imaging system with a computer can implement the method.

10 Claims, 3 Drawing Sheets

U.S. PATENT DOCUMENTS

| | | | | |
|---|---|---|---|---|
| 6,768,811 B2* | 7/2004 | Dinstein et al. | | 382/128 |
| 6,961,606 B2* | 11/2005 | DeSilets et al. | | 600/415 |
| 7,006,881 B1* | 2/2006 | Hoffberg et al. | | 700/83 |
| 7,016,522 B2* | 3/2006 | Bani-Hashemi | | 382/131 |
| 7,123,760 B2* | 10/2006 | Mullick et al. | | 382/131 |
| 7,378,660 B2* | 5/2008 | Case et al. | | 250/363.01 |
| 7,639,892 B2* | 12/2009 | Sheraizin et al. | | 382/274 |
| 7,648,242 B2* | 1/2010 | Ferguson et al. | | 351/221 |
| 7,778,452 B2* | 8/2010 | Jan et al. | | 382/128 |
| 7,795,591 B2* | 9/2010 | Welch | | 250/363.04 |
| 2002/0114500 A1* | 8/2002 | Faber et al. | | 382/128 |
| 2004/0017935 A1* | 1/2004 | Avinash et al. | | 382/131 |
| 2004/0179738 A1* | 9/2004 | Dai et al. | | 382/218 |
| 2005/0027187 A1* | 2/2005 | Barth et al. | | 600/407 |
| 2005/0251036 A1* | 11/2005 | Abuhamad | | 600/437 |
| 2005/0271300 A1* | 12/2005 | Pina | | 382/294 |
| 2006/0098897 A1* | 5/2006 | Dewaele | | 382/294 |
| 2006/0133694 A1* | 6/2006 | Dewaele | | 382/294 |
| 2006/0188134 A1* | 8/2006 | Quist | | 382/128 |
| 2007/0014464 A1* | 1/2007 | Ohashi | | 382/131 |
| 2007/0127845 A1* | 6/2007 | Fu et al. | | 382/294 |
| 2008/0080788 A1* | 4/2008 | Nord et al. | | 382/294 |
| 2008/0146919 A1* | 6/2008 | Camus et al. | | 600/437 |
| 2008/0147086 A1* | 6/2008 | Pfister et al. | | 606/130 |
| 2008/0159607 A1* | 7/2008 | Littmann | | 382/128 |
| 2009/0257628 A1* | 10/2009 | Ranga et al. | | 382/128 |
| 2010/0012848 A1* | 1/2010 | Welch | | 250/363.04 |
| 2010/0308228 A1* | 12/2010 | Vija et al. | | 250/363.04 |

OTHER PUBLICATIONS

Thompson et al. "Mapping adolescent brain change reveals dynamic wave of accelerated gray matter loss in very early onset schizophrenia" Laboratory of Neuro Imaging, NIH, Jul. 18, 2001, pp. 1-6.*

"The Boundary Shift Integral: An Accurate and Robust Measure of Cerebral Volume Changes from Registered Repeat MRI," Freeborough et al. IEEE Trans. on Medical Imaging, vol. 16, No. 5, (Oct. 1997), pp. 623-630.

* cited by examiner

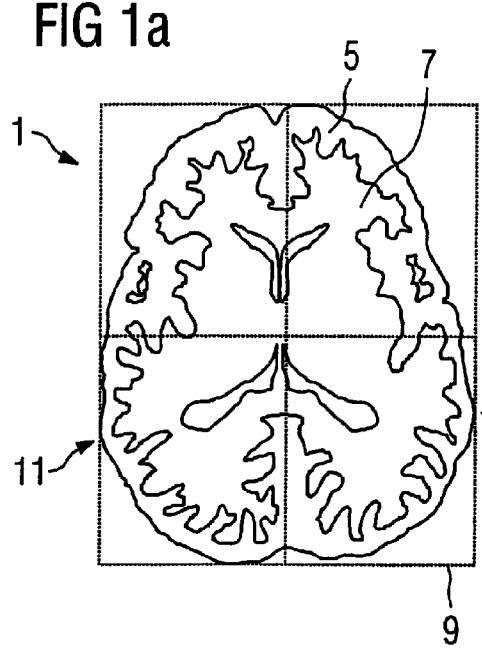
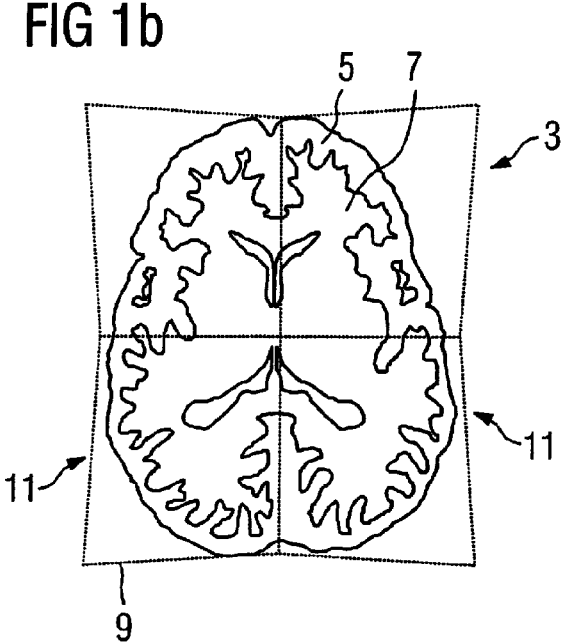
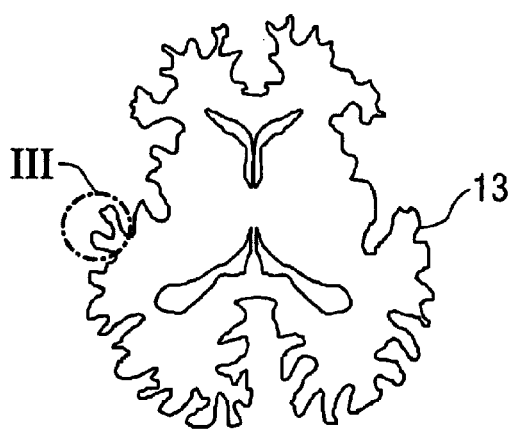
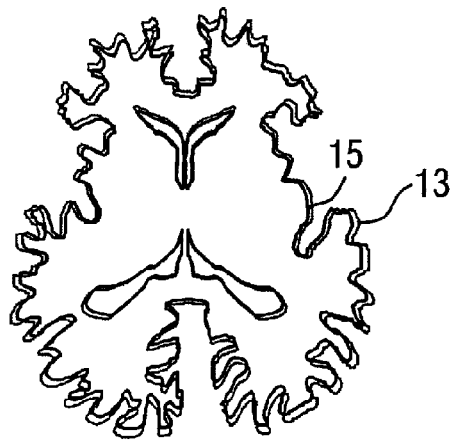
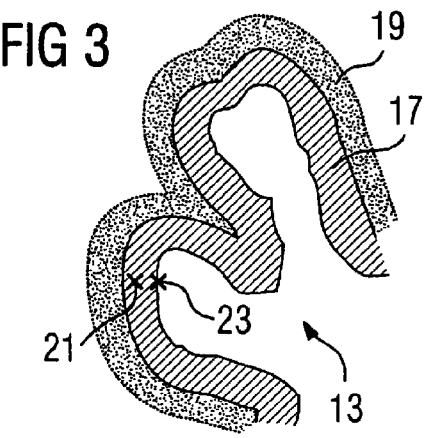

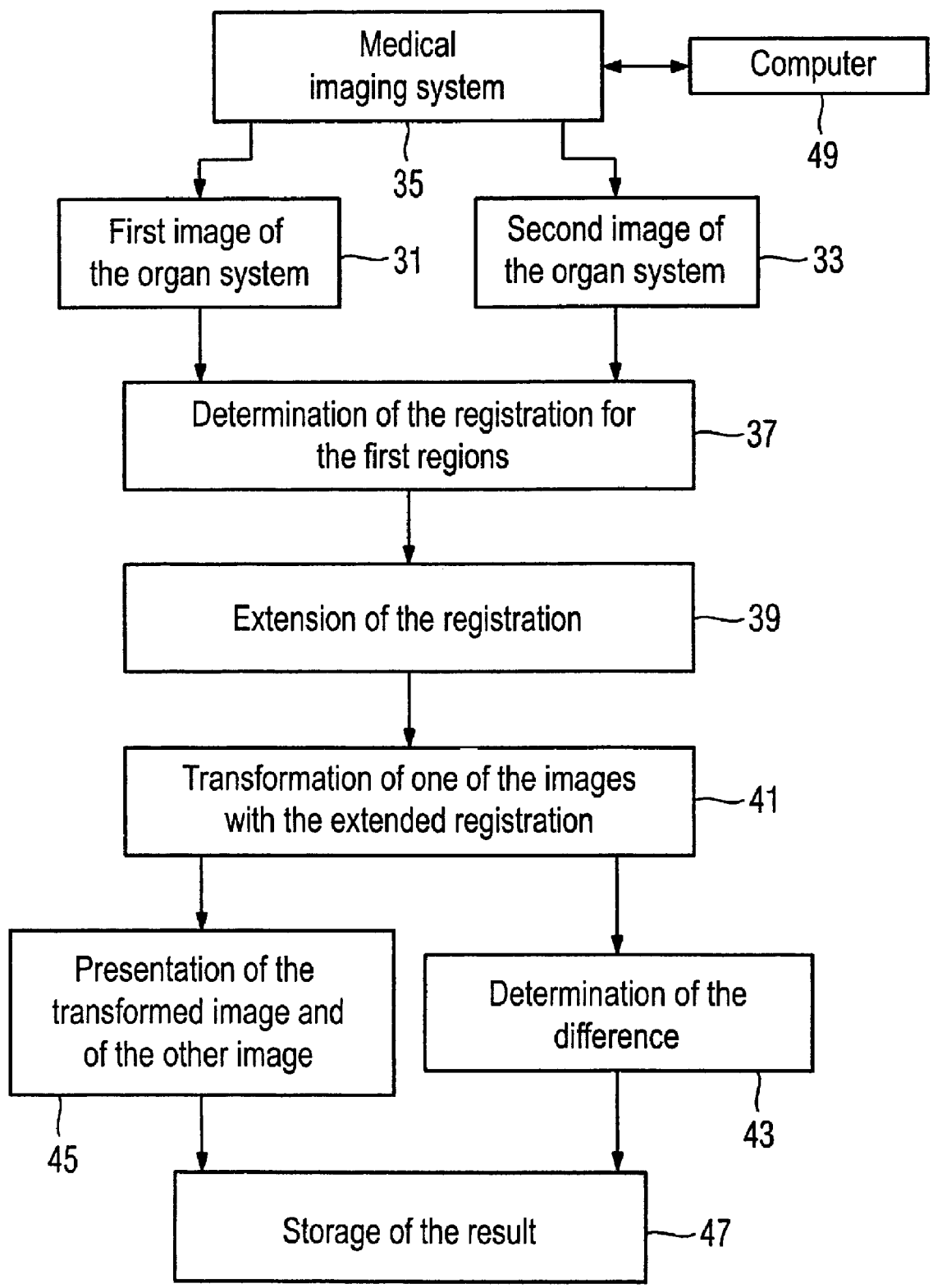

METHOD AND SYSTEM FOR EVALUATING TWO TIME-SEPARATED MEDICAL IMAGES

BACKGROUND OF THE INVENTION

1. Field of the Invention

The present invention concerns a method for evaluation of two corresponding images of an organ acquired at different points in time as well as a medical imaging system for the same purpose.

2. Description of the Prior Art

Longitudinal imaging examinations are necessary for clarification of many medical questions. This means that an organ, organ system or body part to be examined is imaged multiple times at different points in time with the same imaging method. For example, the progression of a specific illness can be determined via a comparison of the images of the organ. Often specific diseases (primarily degenerative illnesses) can only be detected or at least supported via a change that manifests in an organ over the course of time.

One example of such an illness is Alzheimer's disease. This illness can be diagnosed only with difficulty with conventional examination methods, in particular when it is in its early stage. This illness is among the neurodegenerative illnesses and it is known that an atrophy in specific brain regions appears over the course of the Alzheimer's disease due to the loss of nerve cells in, among other places, the grey brain matter (also called the cerebral cortex) of the parietal lobe and temporal lobe.

Although the occurrence of these changes is a known fact, imaging methods (particularly MRT (magnetic resonance tomography) are only very conditionally suitable for diagnoses of Alzheimer's disease, even when volumetric methods are used for measurement of the size of specific cortical regions. This is partially due to the fact that dimensions of the atrophy to be measured and detected lie quantitatively below the inter-individual fluctuation range of the size of specific brain regions.

One possibility to counteract this is to examine the brain of a patient at various points in time and to establish the progression of the atrophy through a comparison of the images. This method, however, has the disadvantage that the differences to be detected cab be very slight, such that a diagnostician who compares the images can easily overlook the differences.

Moreover, when images have been produced by means of MRT methods (typical in neurology) the images exhibit the peculiarity that the images produced at different points in time can exhibit different distortions (particularly deformations). This is due to the fact that MRT methods, in which different magnetic fields that are precisely tuned to one another are used for imaging in a known manner, react sensitively to interfering influences. Therefore, even if care is taken to ensure precisely the same acquisition conditions when the respective images are acquired, the different respective images still will not always exhibit the same (and therewith comparable) geometric deformations. Only the geometric deformations were detected and compensated by means of measurements of a phantom produced before the acquisition could the geometric deformations be better compensated. This is not done in practice, however, due to the large effort and the costs that would be associated therewith.

It is therefore normally not possible for a diagnostician to decide whether the slight but diagnostically relevant differences in the various images are to be ascribed to a geometric deformation or to an actual change of the anatomical conditions in an organ. Due to these facts, MRT examinations previously have not belonged to the recognized and established methods of Alzheimer's diagnostics, but rather are primarily used for exclusion of other illnesses.

Various approaches have been proposed in order to counter the aforementioned problems. A method for measurement of volume changes given repeated three-dimensional MRT acquisitions is disclosed in the article by Freeborough, P. A., Fox N. C., "The boundary shift integral: an accurate and robust measure of cerebral volume changes from registered repeat MRI", IEEE Trans. Med. Imaging 1997; 16: 623-629. The MRT exposures produced at different points in time are rigidly aligned relative to one another and their intensity value differences are integrated. Volume differences of the entire brain can in fact be detected with this method, but this method does not take into account different geometric deformations. Additionally, volume changes cannot be associated with specific brain regions, such that this method often provides a diagnostician with insufficient assistance in the finding or exclusion of a specific diagnosis.

Modifications of this method are known wherein only specific brain regions are examined in order to obtain at least a rough localization of the morphological variations, but here as well geometric deformations are not taken into account.

Although the above problem has been described in the context of Alzheimer's disease and its diagnosis by means or MRT, similar problems exist in the case of other medical questions. The progress of a tumor illness or osteoporosis is one example. The problems of a geometric deformation illustrated above likewise arise predominantly in an MRT examination; however, other examination modalities (such as, for example, computed tomography) can also exhibit similar problems, for example given an incorrect calibration.

SUMMARY OF THE INVENTION

An object of the present invention is to provide a method with which a diagnostician is supported in an effective manner in the evaluation of two images of an organ that were acquired at different points in time. In addition, it is an object of the invention to provide a medical imaging system that supports a diagnostician in an effective manner in the evaluation of two images of an organ that were acquired at different points in time.

The inventive method for evaluation of two corresponding images of at least one organ system acquired at different points in time to establish a pathological variation in a medical clinical image, wherein the at least one organ system exhibits a first region and a second differentiable region in the images of the first region, and wherein the second region of the pathological variation is acquired more strongly than the first region in the medical clinical image, includes the following steps:

determination of a registration for the first region that causes the first region of the first image and the first region of the second image to be in registration with one another as a result of the registration, extension of the registration for the first region to an extended registration such that the second region is encompassed as well via the extended registration, transformation of one of the two images using the extended registration, depiction of the transformed image and of the other image and/or determination of a difference in the two images in the second region via comparison of the second region of the transformed image and of the second region of the other image.

The inventive method utilizes the fact that the pathological variation of the second region is detected more strongly than the first region. Conclusions about imaging system-dependent distortions can now be drawn via a comparison of the first region (that is less strongly affected by the pathological variation) in the two images. The imaging system-dependent distortions can be detected with great precision via the comparison of the first region in one of the two images with the first region in the other image, particularly when the pathological variation in the first region is smaller than the distortions that typically occur in the imaging system with which the images were acquired.

In the inventive method this ensues by a determination of a registration for the first region that causes the first region of the first image and the first region of the second image to be in registration with one another. This means that the transformation is determined that brings the first region of the first image and the first region of the second image largely into congruence with one another.

After the first region in the one image and the first region in the other in registration with one another by the determination of the registration and imaging system-dependent distortions in the first region are thereby known, and as the registration that exists for the first region is extended to an extended registration so that the second region can be detected as well by the extended registration.

Imaging system-dependent distortions (in particular deformations) in the second regions are largely removed in this manner, such that the remaining differences can be ascribed to the pathological variation. Only if the imaging system-dependent distortions were to locally vary significantly in the image might the method reach its limits, since in this case the imaging system-dependent distortions in the second region cannot be determined from the distortions of the first region. Severe, locally varying distortions are, however, typically not expected given the imaging systems presently used.

The extended registration is now used in order to transform both images.

After the transformation of one of the two images has occurred, the remaining difference between the two images, which predominantly appears in the second region, can be shown and/or determined in various ways. Both images (thus the transformed image and the other image) can be presented to the user (diagnostician) in a particularly simple manner so that the user can intuitively recognize the difference by a visual comparison of the two images. The user also can be supported in the determination of the difference by implementing the determination of the difference automatically or semi-automatically and the determined difference is presented. For example, both images can be subtracted from one another so that the difference between the two images is thereby determined. The determined difference can then be presented, for example in the form of a subtraction image, or the determined differences can be marked in the display of the images.

The determined differences or the two images (of which one is transformed) are typically subsequently stored in a storage medium.

The method is preferably applied when the first region of the pathological variation is essentially not detectable in the first region of each image. When the condition is not detectable (i.e. essentially not present) in the first region, the first region remains essentially constant from image-to-image so that—in the event that differences in the representation of the first region should occur in the two images acquired at the different points in time—these differences are to be ascribed to the imaging system with which the images have been produced. These imaging system-dependent differences can now be determined particularly precisely by the registration of the first region in the one image with the first region in the other image.

The registration is preferably determined only for the first region in the determination of the registration for the first region. The registration can be determined more simply, quickly and effectively in this manner, since only the first region of the one image is set in relation to the first region of the other image.

The registration for the first region is advantageously a non-linear registration. The use of a non-linear registration can more precisely detect imaging system-dependent differences, such that the precision of the method is increased.

In a preferred embodiment of the method, the first region that is imaged in one of the images is enlarged in the extension of the registration and the registration for the first region is expanded to the enlarged first region. The extension of the registration is carried out in two sub-steps. In the first step, only the enlargement of the first region occurs, and the registration for image points in the enlarged first region is only determined in the second sub-step. The division into two sub-steps has the advantage that the individual sub-steps can be implemented more simply since known algorithms exist for this purpose.

The enlargement of the first region can be implemented, for example, by an inflation of the first region, for example in a simple manner with a morphological image processing operator for dilatation, for example with what is known as a dilatation filter. It is also possible to effect the enlargement by a scaling, in particular for a first region that is convex.

Various methods can likewise be used in the expansion of the registration to the enlarged first region. For example, for an image point in the enlarged first region it is possible to associate the image point lying nearest that image point from the first region, and to thereupon transfer the registration that is known for the nearest image point of the first region to the image point in the enlarged region. In another variant the registration of the first region can be extrapolated to the enlarged first region.

The enlargement of the first region with subsequent expansion of the registration is advantageously done iteratively in the extension of the registration. The sub-steps of the enlargement of the first region with subsequent expansion of the registration can be fashioned more simply via the iterative extension of the registration since the extension of the registration such that the second region is also encompassed as well now does not need to be provided for in a single step. The second region can also be acquired by successive and repeated application of the extension in this manner.

In a preferred embodiment of the method the first region is segmented before the determination of the registration for the first region. The location of the registration that registers the first regions in the two images with one another, i.e. the determination of the transformation which brings the first regions in the two images into best possible spatial congruence with one another, can be supported in this manner using the previously-effected segmentation.

The two images are advantageously three-dimensional images of the organ system produced with a magnetic resonance apparatus or with a computed tomography apparatus. The registration of the first regions and the extension of the registration can be implemented more precisely and effectively with the use of three-dimensional images since all three dimensions can be taken into account and deformations in all spatial directions can be detected and compensated. Particularly distortions that can occur in magnetic resonance images due to magnetic field inhomogeneities thus can be detected in an effective manner and taken into account in the evaluation of the images.

In a preferred embodiment of the method the organ system is the brain of a patient. The application of the method to images of the brain is particularly advantageous since variations to be detected in the brain are often of small dimensions that, however, are of high diagnostic significance when present.

The first region is preferably white brain matter and the second region is grey brain matter. The slight variations in neurodegenerative processes (such as, for example, occur in the grey brain matter in the case of Alzheimer's disease) can be detected in this manner.

The points in time at which the two corresponding images are acquired can exhibit an interval of one to twelve months, preferably three to six months. This time span is advantageous in the diagnosis of many pathologies of the brain, in particular given neurodegenerative illnesses.

The inventive medical imaging system has a computer that is fashioned for implementation of the method described above.

DESCRIPTION OF THE DRAWINGS

FIG. 1a and FIG. 1b respectively show a transversal section through a brain that has been acquired at different points in time.

FIG. 2a and FIG. 2b show the respective regions of brain white matter tracts belonging to the transverse slices with a superimposition of both regions.

FIG. 3 is a section from FIG. 2a in which two dilatation regions are plotted in addition to the region of the brain white matter tracts.

FIG. 6 is a schematic diagram of the individual method steps that are implemented in an embodiment of the method.

DESCRIPTION OF THE PREFERRED EMBODIMENTS

Figure 4:
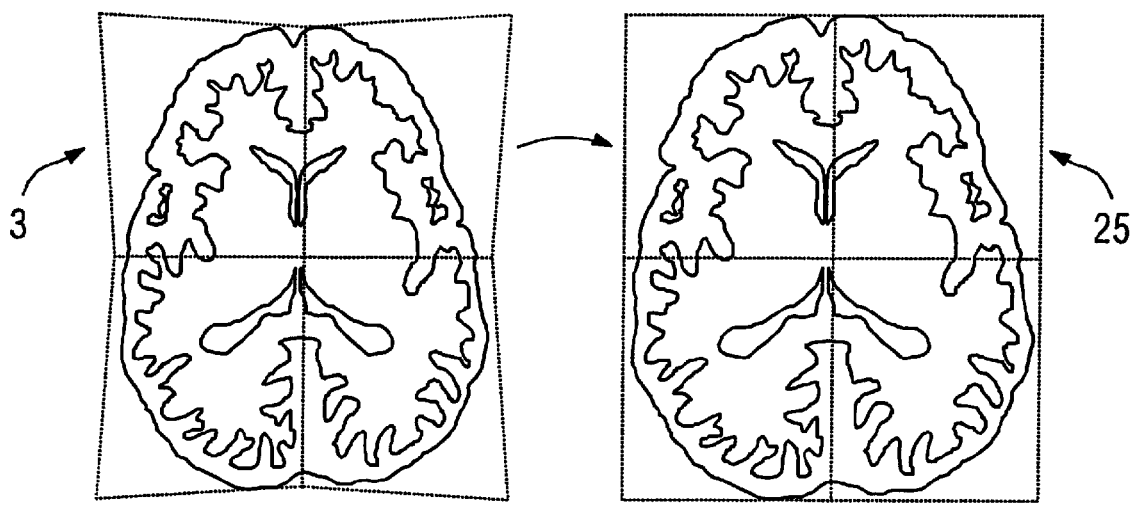
FIG. 4 illustrates a transformation of the second transverse slice with the aid of a determined registration.

The inventive method is illustrated and explained in images of the human brain using FIG. 1 through FIG. 5. FIG. 6 shows a schematic overview of the individual method steps.

FIG. 1a and FIG. 1b show a first transverse slice 1 and a second transverse slice 3 of a brain at the same position. The two transverse slices are each obtained from a 3D volume data set that has been acquired with an MRT apparatus. In the 3D volume data sets the cerebral cortex 5 (or grey brain matter) and the brain white matter tracts (or white brain matter) are imaged distinctly demarcated from one another.

The two 3D volume data sets have been produced at different points in time. A typical question for which such 3D volume data sets are acquired can be, for example, whether indications of Alzheimer's disease are present. In this case the 3D volume data sets are advantageously acquired at a temporal interval of three to six months.

In comparison to the first transverse slice 1, the second transverse slice 3 exhibits a non-uniform geometric deformation. This deformation is indicated in FIG. 1a and FIG. 1b by the shown rectangles 9. Such rectangles 9 here serve only for illustration of the distortion that is otherwise difficult to detect and see and are not visible in images as they typically exist.

The deformation of the second transverse slice 3 can be due to different causes. In magnetic resonance apparatuses it is for the most part to be ascribed to a slight variation of the magnetic fields (which are applied to produce the image) that occurs during the operation. The deformations that occur can be in the millimeter range. Other causes can also be responsible for this, for example an incorrect or altered calibration of the medical imaging system.

When a user would like to evaluate the two transverse slices, the user is confronted with the problem that the user can presume variations of the cerebral cortex in the temporal region 11, since here the cortex appears narrower in the transverse slice 3 than in the first transverse slice 1. Ultimately, however, the user cannot be sure since the variations can at least in part also be ascribed to the deformations.

However, since Alzheimer's disease is an illness in which the degenerative processes primarily lead to a volumetric change in the cortex 5 while the white matter tracts 7 remain largely morphologically unchanged, the deformation can be determined via a comparison of the white matter tracts 7. This step is now explained in FIG. 2a and FIG. 2b.

The white matter tract region (designated in the following as the first white matter tract region 13 and the second white matter tract region 15) is first respectively extracted from the first transverse slice 1 and the second transverse slice 3. Since the white matter tracts 7 are clearly delimited from the cortex 5 in the 3D volume data set, this can be done, for example, using methods that identify the white matter tracts 7 based on the specific signal intensity of the individual voxels. Other typical automatic or semi-automatic segmentation algorithms can also be applied. For example, a user can click in a central region of the white matter tracts 7 and thus initiate a segmentation algorithm that, starting from the selected start point, finds the contour of the contiguous white matter tracts 7.

The first white matter tract region 13 and the second white matter tract region 15 exhibit distortion-dependent differences. This is clearly shown in FIG. 2b in the second white matter tract region 15, since here the first white matter tract region 13 is shown superimposed and dotted so that the distortion is clearly visible.

A registration that transforms the first and second white matter tract regions 13, 15 into one another is determined by a comparison of the first white matter tract region 13 with the second white matter tract region 15. This means that, using the registration for every pixel of the first white matter tract region 15, a transformation vector is known that associates a corresponding point of the second white matter tract region 15 with this point, and vice versa.

The type of registration that is selected is predominantly adapted to the medical imaging system and represents a compromise between precision of the registration and computation time for determination of the registration. For imaging systems in which, for example, cumulatively only an affine deformation occurs, it can suffice to merely determine an affine registration that sets the two regions in a best possible relation to one another. In other imaging systems (such as, for example, in an MRT apparatus) in which image regions are predominantly non-linearly deformed, this can be utilized to determine the matching non-linear registration. The matching registration also can be successively determined by, for example, a rigid or affine registration is determined first, and then a non-linear registration is determined based thereon.

By the registration of the two white matter tract regions 13, 15 it is now known how image points of the first white matter tract region 13 coincide with the second white matter tract region 15 or—expressed otherwise—for each image point of the one white matter tract region a transformation vector is known that maps this image point to the corresponding image point of the other white matter tract region.

After the registration was found that transforms the first and second white matter tract regions 13, 15 into one another, the registration is expanded to further regions. For this purpose, the first (or the second) white matter tract region 13 is dilated (i.e. enlarged) in a first step. This enlargement can be implemented, for example, in a simple manner using a morphological image processing operator for dilatation. In a second step, transformation vectors can be associated with the pixels of the dilated region that were not yet detected by the registration (since the registration was only effected for the first and second white matter tract regions 13, 15), as explained in the following using FIG. 3.

FIG. 3 shows a section from the first white matter tract region 13 corresponding to the rectangle III in FIG. 2a. In addition to the first white matter tract region 13, a first dilatation region 17 is plotted. The first dilatation region 17 thereby arises from a dilatation of the first white matter tract region 13.

The pixels of the first dilatation region 17 all lie near the first white matter tract region 13. A transformation vector is now associated with a pixel 21 that lies in the first dilatation region 17 and that is not yet recorded by the registration. For example, the transformation vector of the nearest pixel 23 from the first white matter tract region 13 can be associated with this pixel 21. Alternatively, an averaging, (possibly weighted), of transformation vectors of a number of pixels of the white matter tracts 13 that lie near the pixel 21 can also be associated. Alternatively, the transformation vector for the pixel 21 that lies in the first dilatation region 17 can be determined from an extrapolation of the transformation vectors for pixels of the first brain white matter tract region 13. In all cases the registration is extended or extrapolated from the first white matter tract region 13 to the first dilation region 17.

After the registration has been extended to the first dilatation region 17, this extension can be iteratively re-implemented so that the extension now also encompasses a second dilatation region 17 and successive further regions until regions that image the cortex 5 are also encompassed.

The extended registration has the advantage that it does in fact transform into one another the regions using which it was determined (thus in this case the white matter tracts 7) such that they substantially coincide. However, the remaining regions (thus the cortex 5 in this case) are altered by the extended registration only insofar as that deformation-dependent distortions are compensated. The variations that are to be ascribed to an alternation of the anatomical ratios of the remaining regions are not compensated by the registration, such that this information is retained given an application of the registration.

The registration shown here was determined by a comparison of the first and second white matter tract regions 13, 15 of the first and second transverse slices 1, 3, i.e. by a comparison of two two-dimensional images. However, the determination of the registration is not limited to two-dimensional slice images. The extraction of the white matter tracts 7 can also ensue in the entire 3D volume data set, such that the three-dimensional structure of the brain white matter tracts 7 is also known. The registration can ensue by a comparison of both three-dimensional structures of the brain white matter tracts 7.

The use of three-dimensional structures for determination of the registration has the advantage that deformations that result in the direction of the sequence of the individual transverse slices are also detected in this manner. A more precise registration results that transforms the one 3D volume data set and the other 3D volume data set into one another.

After the extension of the registration, one of the two transverse slices (in this case the second transverse slice 3) can be transformed with the registration as shown in FIG. 4. When the transformed second transverse slice 25 is now compared with the first transverse slice 1, the first and the second white matter tract regions 13, 15 that were starting points for the registration are largely congruent. By contrast, in the cortex 5 only deformation-dependent differences were largely corrected by the registration while the differences that result due to a pathological change remain for the most part. For example, the second transformed transverse slice 25 and the first transverse slice 1 can be shown in parallel to the user in a particularly simple manner. In that imaging system-dependent distortions are now compensated, the user can direct his attention to differences between the two images that are now to be ascribed to pathological changes.

Figure 5:
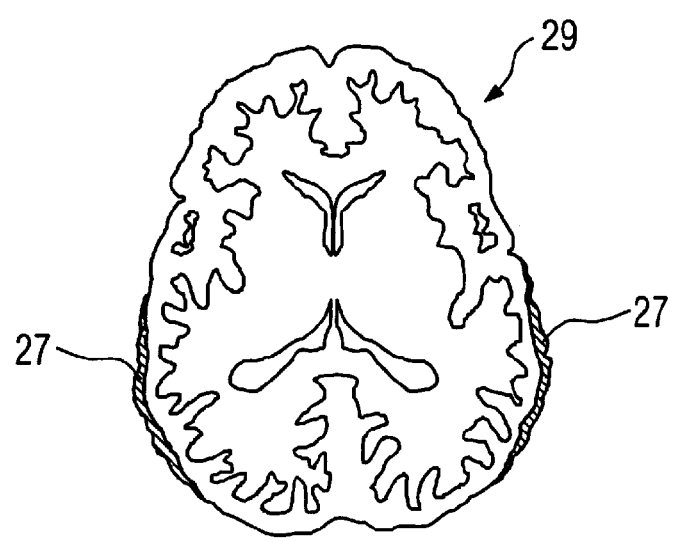
FIG. 5 illustrates a superimposed representation of the first transformed transverse slice and the second transformed transverse slice.

Pathological changes are clearly visible due to a superimposed presentation 29 of the transformed second transverse slice 25 with the first transverse slice 1 as shown in FIG. 5. The differences 27 between the two transverse slices can now be visualized in a simple manner, for example by a subtraction of the first transverse slice 1 and the transformed second transverse slice 25 or by color identification of the differences 27. Evaluation methods that quantitatively determine the dimensions of the change, for example via a volumetric measurement, can likewise follow in connection with the determination of the differences.

However, the method steps explained here in FIG. 1 through FIG. 5 using MR images of the brain are not limited to the specific organ system, the specific imaging modality or the specific medical question shown in FIG. 1 through FIG. 5. An average person skilled in the art can likewise apply the method in other imaging modalities and in other medical questions in which an organ system has first and second regions that present themselves as differentiable in an image and in which a pathological change predominantly manifests in one of the two regions while the other region remains essentially unaffected by the pathological change and constant.

In summary, FIG. 6 shows a scheme of the individual method steps that are executed in the implementation of the method.

A first image 31 and a second image 33 of an organ system that corresponds to the first image 31, which images were respectively acquired with a medical imaging system 35 at different points in time, are the starting point of the method. The organ system has a first region and a second region that respectively appear differentiable in the two images 31, 33.

In both of these images 31, 33 the possible occurrence of a pathological change that belongs to a medical clinical image should be detected by the method. Of the pathological change it is known that it only causes a change in the second region of the organ system while the first region is not encompassed by a pathological change in the clinical image.

A registration for the first regions is determined in a first method step 37, such that the first region of the first image 31 and the first region of the second image 33 are registered with one another by the registration.

The registration via which until now only the first regions in both images have been registered with one another is extended in a second method step 39 so that the second region of both images is also encompassed by this extension of the registration.

In a third method step 41, one of the two images is transformed using the extended registration in order to automatically or semi-automatically determine in a fourth method step 43 a difference of the two images in the second region via comparison of the second region of the transformed image and the second region of the other image.

Alternatively, in a fifth method step 45 the transformed image and the other image are presented in parallel to a user so that the user can determine the difference between the two images via visual observation of both images.

In a sixth method step 47, the results of the method (thus the determined difference and/or the transformed image and the other image) are stored on a storage medium.

The method is advantageously implemented by a computer 49 that is connected with the medical imaging system since such a computer 49 often has image evaluation and image presentation functions that can be advantageously used in the method to be implemented.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for assisting evaluation of first and second images, respectively acquired at different points in time, of an organ system, said first and second images containing corresponding representations of said organ system with said organ system, in each of said first and second images, exhibiting a first region and a differentiatable second region representing a pathological condition, with said pathological condition being represented more strongly in said first region of each of said first and second images, said method comprising the steps of:

automatically electronically determining a registration procedure that brings only the respective first regions in the first and second images into registration with each other;

extending said registration procedure determined for said first region to encompass said second region in said first image by enlarging said first region in one of said first and second images and expanding the registration of said first region in said first image with said first region in said image corresponding to the enlarged first region, thereby obtaining an extended registration in said first image;

transforming said second image by applying said extended registration thereto to cause said second region in said second image to conform to the second region in said first image according to said registration procedure, thereby obtaining a transformed second image; and automatically presenting an evaluation result that establishes a change in said pathological condition between said respective points in time, said result being selected from a group consisting of visually presenting said transformed second image simultaneously with the image with the extended registration, and automatically determining a difference image between said transformed second image and said image with the extended registration.

2. A method as claimed in claim 1 wherein said change in said pathological condition is represented in said first and second images only in said second region.

3. A method as claimed in claim 1 comprising determining said registration procedure as a non-linear registration of said first region in each of said first and second images.

4. A method as claimed in claim 1 comprising iteratively enlarging said first region.

5. A method as claimed in claim 1 comprising segmenting said first region before determining said registration procedure.

6. A method as claimed in claim 1 comprising employing three-dimensional images of said organ system, generated with an imaging modality selected from the group consisting of a magnetic resonance apparatus and a computed tomography apparatus, as said first and second images.

7. A method as claimed in claim 1 comprising employing first and second images of the brain of a patient as said organ system in said first and second images.

8. A method as claimed in claim 7 wherein said first region represents white brain matter and wherein said second region represents gray brain matter.

9. A method as claimed in claim 7 comprising acquiring said first and second images at an interval in a range between three to six months from each other.

10. A medical image evaluation system for assisting evaluation of first and second images, respectively acquired at different points in time, of an organ system, said first and second images containing corresponding representations of said organ system with said organ system, in each of said first and second images, exhibiting a first region and a differentiatable second region representing a pathological condition, with said pathological condition being represented more strongly in said first region of each of said first and second images, said system comprising:

a computer configured to automatically determine a registration procedure that brings only the respective first regions in the first and second images into registration with each other, and to extend said registration procedure determined for said first region to encompass said second region in said first image by enlarging said first region in one of said first and second images and expanding the registration of said first region in said first image with said first region in said image corresponding to the enlarged first region, thereby obtaining an extended registration in said first image, and to transform said second image by applying said extended registration to said second region in said second image cause said region in said second image to conform to said second region in said first image, thereby obtaining a transformed second image, and to automatically generate an evaluation result that establishes a change in said pathological condition between said respective points in time, said result being selected from a group consisting of generating first display data to simultaneously visually present said transformed second image and the first image with the extended registration, and generating second display data representing a difference image between said transformed second image and said first image with the extended registration; and a display unit in communication with said computer that displays said evaluation result.

* * * * *